United States Patent
Clifton et al.

(10) Patent No.: US 9,454,817 B2
(45) Date of Patent: Sep. 27, 2016

(54) RELATING TO IMAGE PROCESSING

(71) Applicant: Optos PLC, Dunfermline (GB)

(72) Inventors: David Clifton, Shandon (GB); Ralph Allen Pinnock, Dunfermline (GB)

(73) Assignee: OPTOS PLC, Dunfermline (GB)

(*) Notice: Subject to any disclaimer, the term of this patent is extended or adjusted under 35 U.S.C. 154(b) by 0 days.

(21) Appl. No.: 14/654,249

(22) PCT Filed: Feb. 19, 2014

(86) PCT No.: PCT/GB2014/050480
§ 371 (c)(1),
(2) Date: Jun. 19, 2015

(87) PCT Pub. No.: WO2014/128456
PCT Pub. Date: Aug. 28, 2014

(65) Prior Publication Data
US 2015/0324966 A1    Nov. 12, 2015

(30) Foreign Application Priority Data
Feb. 19, 2013    (GB) .................................. 1302887.3

(51) Int. Cl.
*G06K 9/00*    (2006.01)
*G06T 7/00*    (2006.01)
(Continued)

(52) U.S. Cl.
CPC ............. *G06T 7/003* (2013.01); *A61B 3/0025* (2013.01); *G06T 5/20* (2013.01); *G06T 7/0026* (2013.01); *A61B 3/1225* (2013.01); *G06T 2207/20148* (2013.01); *G06T 2207/20164* (2013.01); *G06T 2207/30041* (2013.01); *G06T 2207/30101* (2013.01)

(58) Field of Classification Search
None
See application file for complete search history.

(56) References Cited

U.S. PATENT DOCUMENTS
2012/0195481 A1    8/2012    Gonzalez Penedo et al.

FOREIGN PATENT DOCUMENTS
EP    2064988 A1    6/2009

OTHER PUBLICATIONS
Can, Ali, et al.; "A Feature-Based, Robust, Hierarchical Algorithm for Registering Pairs of Images of the Curved Human Retina"; IEEE Transactions on Pattern Analysis and Machine Intelligence, vol. 24, No. 3; Mar. 2002; pp. 347-364.
(Continued)

*Primary Examiner* — Atiba O Fitzpatrick
(74) *Attorney, Agent, or Firm* — Christopher J. McKenna; Shabbi S. Khan; Foley & Lardner LLP (57) ABSTRACT

An image processing apparatus uses first and second digital vascular image data to register two images. The two images may be from different imaging modes. The first and second images are processed with a two-dimensional, directional filter (500) that has the effect of producing clusters of orthogonally adjacent image data points in which the magnitude of an intensity gradient between each orthogonally adjacent image data point is less than a predetermined value. Subsequently, common clusters are identified between the first and second image data using a corner detecting algorithm (600). The directional filter produces "stepping" features, where vascular features would otherwise appear with smooth edges. These numerous features are identified by the corner detecting algorithm and can be used (1000) for registering common clusters between the first and second image data. The filter may be a rotating Gabor filter matched to vascular features in the images.

25 Claims, 10 Drawing Sheets

(51) Int. Cl.
*G06T 5/20* (2006.01)
*A61B 3/00* (2006.01)
*A61B 3/12* (2006.01)

(56) References Cited

OTHER PUBLICATIONS

Zana, F., et al.; "A Multimodal Registration Algorithm of Eye Fundus Images using Vessels Detection and Hough Transform"; IEEE Transactions on Medical Imaging, vol. 18, No. 5; May 5, 1999; pp. 419-428.

Hu, Zhihong, et al.; "Multimodal Retinal Vessel Segmentation from Spectral-Domain Optical Coherence Tomography and Fundus Photography"; IEEE Transactions on Medical Imaging, vol. 31, No. 10; Oct. 10, 2012; pp. 1900-1911.

Li, Qin, et al.; "A Multiscale Approach to Retinal Vessel Segmentation Using Gabor Filters and Scale Multiplication"; 2006 IEEE International Conference on Systems, Man, and Cybernetics; Taipei, Taiwan; Oct. 8-11, 2006; pp. 3521-3527.

Rangayyan, Rangaraj M., et al.; "Detection of Blood Vessels in the Retina using Gabor Filters"; IEEE; Apr. 2007; pp. 717-720.

Ritter, Nicola, et al.; "Registration of Stereo and Temporal Images of the Retina"; IEEE Transactions on Medical Imaging, vol. 18, No. 5; May 1999; pp. 404-418.

Pinz, Axel, et al.; "Mapping the Human Retina"; IEEE Transactions on Medical Imaging, vol. 17, No. 4; Aug. 1998; pp. 606-619.

Abràmoff, Michael D., et al.; "Retinal Imaging and Image Analysis"; IEEE Reviews in Biomedical Engineering, vol. 3; 2010; pp. 169-208.

Klemencic, Ales, International Search Report, prepared for PCT/GB2014/050480, as mailed May 22, 2014, four pages.

RELATING TO IMAGE PROCESSING

TECHNICAL FIELD

The present invention relates to improvements in or relating to image processing, particularly, but not exclusively, to a method and apparatus for registering pairs or sequences of vasculature images, such as retinal images.

BACKGROUND

Imaging systems, such as scanning laser ophthalmoscopes (SLOs), are known to capture retinal image data using one or more digital image sensors. Digital image sensors for SLOs are commonly a single sensor in which the light intensity signal is synchronised with the scanning position signal in order to produce a single stream of data that can be synchronised into a 2D image. Digital image sensors may alternatively include an array of light sensitive picture elements (pixels) Retinal images produced by SLOs or other retinal imaging apparatuses such as fundus cameras are typically two dimensional pixel arrays and are termed digital retinal images.

The set of intensity values derived from the pixel array is known as image data. The "raw" image data output by the pixel array may be subjected to various post-processing techniques in order to reproduce an image either for viewing by a human or for processing by a machine. Post-processing techniques of retinal images include various statistical methods for image analysis and registration of pairs or sequences of retinal images.

Registering pairs or sequences of retinal images generally concerns the scaling, rotation and translation of one or more images with respect to a base image in order to align ("register") the image with the base image. The registered retinal images are typically superimposed with the base retinal image to facilitate comparisons between the images.

Algorithms which enable affine registration of pairs or sequences of retinal images are known. Such algorithms may involve "vasculature tracking", which involves iterative searches and decision trees to map and extract the vasculature. In particular, such approaches commonly search for specific characteristic features such as vasculature branching junctions. While such algorithms provide a reasonable degree of registration accuracy they are computationally inefficient, i.e. computationally expensive. Furthermore, such known algorithms only allow images obtained from common imaging modes to be registered. That is, such known algorithms do not allow images obtained from different imaging modes, such as reflectance or auto-fluorescence, to be registered.

Examples of such known algorithms can be found in the following publications: US 2012/0195481A; Can et al "A feature based, Robust, Hierarchical Algorithm for Registering Pairs of Images of the Curved Human Retina", IEEE Transactions on Pattern Analysis and Machine Intelligence, Vol 24, No, 3 (March 2002); Zana & Klein, "A Multimodal Registration Algorithm of Eye Fundus Images Using Vessels Detection and Hough Transform", IEEE Transactions on Medical Imaging, Vol 18, No 5 (May 1999); and Hu et al "Multimodal Retinal Vessel Segmentation From Spectral-Domain Optical Coherence Tomography and Fundus Photography", IEEE Transactions on Medical Imaging, Vol 31, No 10 (October 2012).

EP 2 064 988 A (Kowa Company, Ltd.) proposes a device and method for creating retinal fundus "maps" by superimposing two or more fundus images on the basis of a matching probability score. Matching is performed on the basis of corner image data identified in a blood vessel extraction image. However, the inventors believe that the technique proposed in EP'988 will not find sufficient corner features in the vasculature in a typical retinal image to enable reliable matching and registration of images, especially between different imaging modes. Retinal images are subject to very variable lighting, and in high-resolution retinal images produced by modern SLOs, the vascular features are relatively smooth-sided features. Therefore corner extraction will not yield a great number of candidate points for matching, or else will be heavily influenced by noise of various types.

SUMMARY

According to a first aspect of the invention there is provided a method of processing digital vascular images comprising the steps of:
  providing first and second digital vascular image data;
  processing the first and second image data with a directional, two-dimensional filter that has the effect of producing clusters of orthogonally adjacent image data points in which the magnitude of an intensity gradient between each orthogonally adjacent image data point is less than a predetermined value;
  identifying clusters in each of the first and second image data where the magnitude of the intensity gradient between one or more adjacent clusters is greater than a predetermined value;
  identifying common clusters between the first and second image data where the magnitude of the intensity gradient between one or more adjacent clusters is greater than a predetermined value; and
  registering the common clusters between the first and second image data.

The digital vascular images may be retinal images. The digital vascular images may include detail of the vasculature of the retina. The vasculature of the retina includes the blood vessels, arteries and veins in the retina. The vasculature of the retina includes the circulatory system of the retina.

The digital vascular images may be vascular images of an organ or body part of a human or an animal. The digital vascular images may include detail of the vasculature of the organ or the body part. The vasculature of the organ or the body part includes the blood vessels, arteries and veins therein. The vasculature of the organ or the body part includes the circulatory system thereof.

The first and second digital vascular image data may include the intensity of the illumination incident on the one or more pixels used to produce the image data. The first and second images may be obtained by different imaging modes.

The filter may be a matched filter. The filter may have a form or shape which is matched to the form or shape of vascular features in the vascular image data.

The filter may be a Gaussian filter. The filter may be a Gabor filter.

The one or more filters may be the same filter or different filters. Using different two-dimensional filter kernels at different orientations may be useful in cases where the vasculature has some shape sensitivity with direction.

The kernel may be a matched kernel. The kernel may have a form or shape which is matched to the form or shape of the vascular image data.

The clusters of orthogonally adjacent image data points may include any number or configuration of orthogonally adjacent image data in which the intensity gradient between each orthogonally adjacent image data point is less than a predetermined value.

The step of identifying clusters in each of the first and second image data where the magnitude of the intensity gradient between one or more adjacent clusters is above a predetermined value may include use of a corner detection algorithm. The corner detection algorithm may be used to identify clusters in each of the first and second image data where the magnitude of the intensity gradient between one or more adjacent clusters is above a predetermined value. The corner detection algorithm may be used to identify clusters in each of the first and second image data where the magnitude of the intensity gradient between one or more adjacent clusters in two orthogonal directions is simultaneously above a predetermined value. That is, the corner detection algorithm may look for changes in intensity gradients occurring simultaneously in two orthogonal directions above a predetermined threshold. The predetermined value may be for example between 10% and 50% of a maximum possible gradient value.

The corner detection algorithm may be a Harris corner detection algorithm. The corner detection algorithm may be a Moravec corner detection algorithm or a Shi-Thomas corner detection algorithm.

The step of identifying common clusters between the first and second image data where the magnitude of the intensity gradient between one or more adjacent clusters is above a predetermined value may include cross correlating the convolved first and second image data.

The step of identifying common clusters between the first and second image data where the magnitude of the intensity gradient between one or more adjacent clusters is above a predetermined value may include cross correlating the identified clusters in the first and second image data.

The step of identifying common clusters between the first and second image data where the magnitude of the intensity gradient between one or more adjacent clusters is above a predetermined value may include multiple cross correlations of the convolved first and second image data. For multiple cross correlations of the convolved first and second image data, each successive cross correlation may be incrementally rotated from the last. The multiple cross correlations may be rotated through approximately 40 degrees, or more. The multiple cross correlations may be rotated in steps through approximately 20 degrees or more around a pivot point located substantially around the optic disc point of the retina.

The step of cross correlating the convolved first and second image data may include the further step of determining the differences in position between the identified common clusters in each of the first and second image data. The position of the cluster may include its angular position and/or its translational position. The differences in position between the identified common clusters in each of the first and second image data may be termed the translational parameters.

The step of registering the common clusters between the first and second image data uses the determined translational parameters to align the first and second image data. The second image data may be registered with the first image data or the first image data may be registered with the second image data. The registered image data may be superimposed.

The method may include the additional initial step of reducing the size of the first and/or second digital vascular image data. This may include removing one or more portions of the image data. The step of reducing the size of the first and/or second digital vascular image data may include the steps of filtering, smoothing, sampling or sub sampling the image data. The steps of filtering, smoothing, sampling or sub sampling the image data may be repeated any number of times.

The method may include the additional initial step of down sampling the first and/or second digital vascular image data. The step of down sampling the first and/or second digital vascular image data may include one or more image data scaling computations. The step of down sampling the first and/or second digital vascular image data may include one or more image data pyramid scaling computations.

The method may include the additional initial step of increasing the contrast between the vasculature and the background of the first and/or second digital vascular image data. The method may include the additional initial step of optimising the contrast between the vasculature and the background of the first and/or second digital vascular image data. The step of optimising the contrast between the vasculature and the background of the first and/or second digital vascular image data may include using a histogram equalisation. The step of optimising the contrast between the vasculature and the background of the first and/or second digital vascular image data may include using an adaptive histogram equalisation.

The method may include the additional step of removing noise from the first and/or second digital vascular image data after the step of increasing the contrast between the vasculature and the background of the first and/or second digital vascular image data. The step of removing noise from the first and/or second digital vascular image data may include use of a low-pass filter.

The method may include the additional step of merging, or linking, together the clusters in each of the first and second image data where the magnitude of the intensity gradient between one or more adjacent clusters is above a predetermined value. The clusters may be "merged" by increasing the intensity data between the clusters. A single pass averaging filter, or kernel, may be used to adjust the intensity value of the image data between clusters to an average intensity value of the clusters in that region. The effect of this is to blur, or average, the intensity values within a given region so that two clusters close together will, in effect, become one cluster.

The method may include the additional step of reducing the size of the first and/or second merged cluster image data. This may include removing one or more portions of the image data. The step of reducing the size of the first and/or second merged cluster image data may include the steps of filtering, smoothing, sampling or sub sampling the image data. The steps of filtering, smoothing, sampling or sub sampling the image data may be repeated any number of times.

The method may include the additional initial step of down sampling the first and/or second merged cluster image data. The step of down sampling the first and/or second merged cluster image data may include one or more image data scaling computations. The step of down sampling the first and/or second merged cluster image data may include one or more image data pyramid scaling computations.

The method may include the additional step of creating first and/or second digital vascular images from the first and second digital vascular image data.

The method may include the additional step of creating a digital image of the first and/or second clusters of orthogonally adjacent image data points in which the intensity gradient between each orthogonally adjacent image data point is less than a predetermined value.

The method may include the additional step of creating a digital image of the identified clusters in the first and/or second image data where the magnitude of the intensity gradient between one or more adjacent clusters is above a predetermined value.

The method may include the additional step of creating a digital image of the identified common clusters between the first and second image data where the magnitude of the intensity gradient between one or more adjacent clusters is above a predetermined value.

The method may include the additional step of creating a digital image of the registered common clusters between the first and second image data.

The method may comprise providing a plurality of digital vascular image data and processing each digital image data according to the first aspect of the invention to register all the common clusters between all the image data.

According to a second aspect of the invention there is provided an image processing apparatus comprising:
 a digital vascular image provision module arranged to provide first and second digital vascular image data; and
 a processor arranged to:
 process the first and second image data with a two-dimensional, directional filter that has the effect of producing clusters of orthogonally adjacent image data points in which the magnitude of an intensity gradient between each orthogonally adjacent image data point is less than a predetermined value;
 identify clusters in each of the first and second image data where the magnitude of the intensity gradient between one or more adjacent clusters is greater than a predetermined value;
 identify common clusters between the first and second image data where the magnitude of the intensity gradient between one or more adjacent clusters is greater than a predetermined value; and
 register the common clusters between the first and second image data.

According to a third aspect of the invention there is provided a scanning laser ophthalmoscope having an image processing apparatus comprising:
 a digital vascular image provision module arranged to provide first and second digital vascular image data; and
 a processor arranged to:
 process the first and second image data with a two-dimensional, directional filter that has the effect of producing clusters of orthogonally adjacent image data points in which the magnitude of the intensity gradient between each orthogonally adjacent image data point is less than a predetermined value;
 identify clusters in each of the first and second image data where the magnitude of the intensity gradient between one or more adjacent clusters is greater than a predetermined value;
 identify common clusters between the first and second image data where the magnitude of the intensity gradient between one or more adjacent clusters is greater than a predetermined value; and
 register the common clusters between the first and second image data.

According to a fourth aspect of the invention there is provided a computer program product encoded with instructions that, when run on a computer, cause the computer to receive image data and perform a method of processing digital vascular images comprising:
 providing first and second digital vascular image data;
 processing the first and second image data with a two-dimensional, directional filter that has the effect of producing clusters of orthogonally adjacent image data points in which the magnitude of the intensity gradient between each orthogonally adjacent image data point is less than a predetermined value;
 identifying clusters in each of the first and second image data where the magnitude of the intensity gradient between one or more adjacent clusters is greater than a predetermined value;
 identifying common clusters between the first and second image data where the magnitude of the intensity gradient between one or more adjacent clusters is greater than a predetermined value; and
 registering the common clusters between the first and second image data.

The computer program product may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fibre optic cable, twisted pair, digital subscriber line (DSL), or wireless technologies such as infrared, radio, and microwave, then the coaxial cable, fibre optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray™ disc where disks usually reproduce data magnetically, while discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

BRIEF DESCRIPTION OF THE DRAWINGS

An embodiment of the invention will now be described, by way of example only, with reference to the accompanying drawings, in which.

DETAILED DESCRIPTION OF EXEMPLARY EMBODIMENTS

Figure 1:
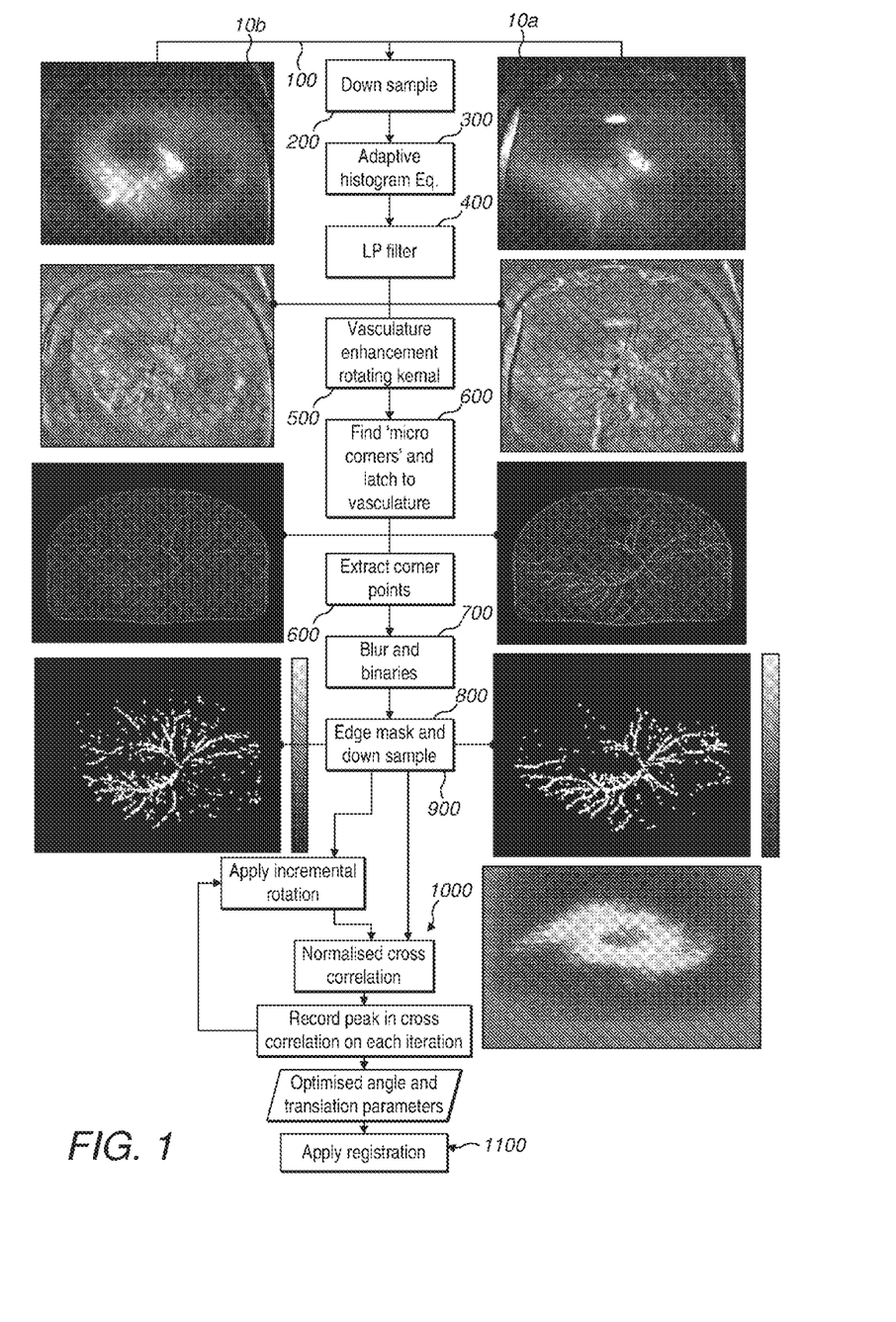
FIG. 1 is a flow chart diagram detailing a method of processing digital vascular images.

FIG. 1 is a flow chart detailing the method steps of a registration algorithm for affine registration of pairs or sequences of retinal images.

FIG. 1 illustrates the method steps of processing the digital retinal image data. The first image may be termed the "base image", with each subsequent image being termed the "input" image.

Figure 2A:
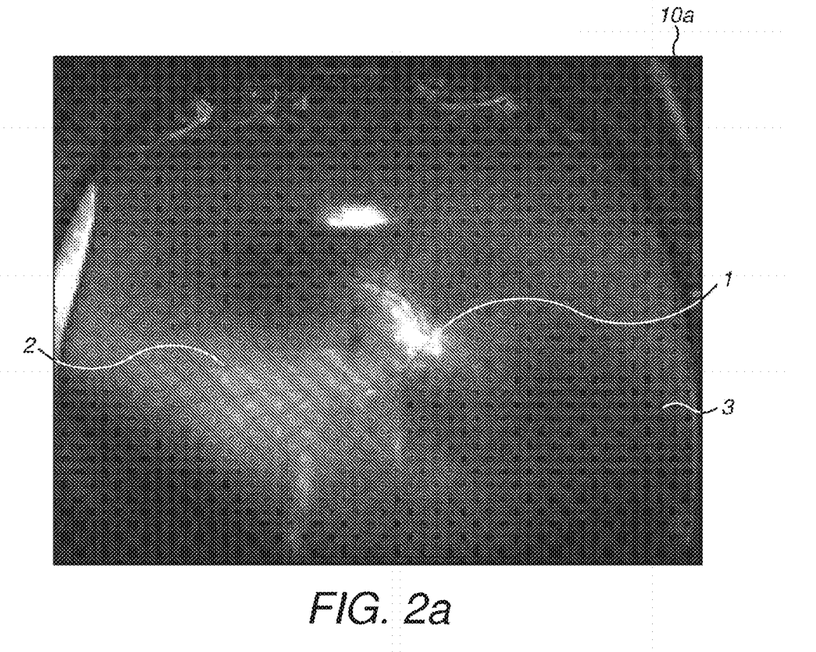
FIGS. 2a and 2b are first and second digital vascular images.
Figure 2B:
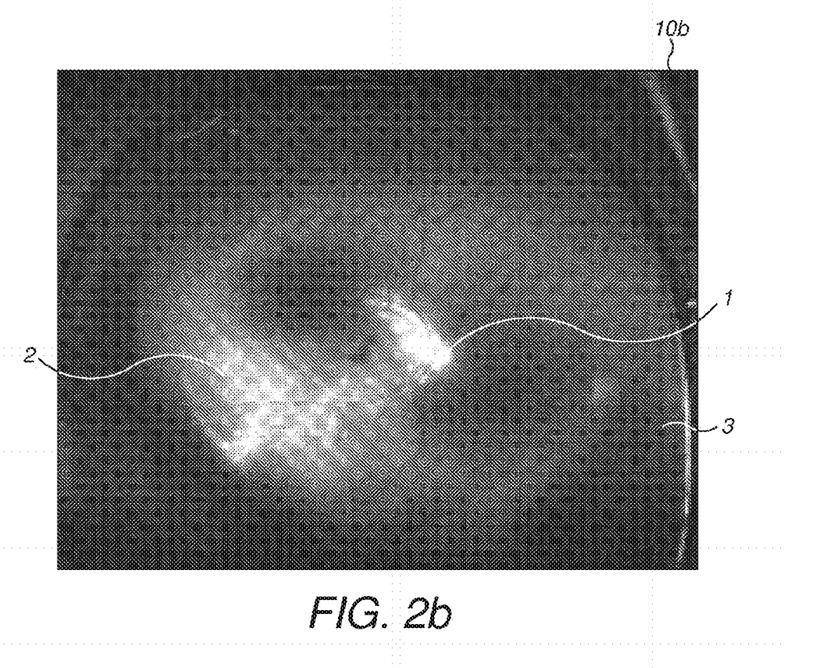

With reference to FIGS. 1, 2a and 2b, the first step 100 of the method is to provide first and second digital retinal image data. The first and second digital retinal image data is represented by first and second digital retinal images 10a, 10b. The first and second digital vascular image data includes the intensity of the illumination incident on the one or more pixels used to produce the image data. The first and second digital retinal images 10a, 10b illustrated here are obtained by a wide-field scanning laser ophthalmoscope (SLO), as is known in the art. As illustrated in FIGS. 2a and 2b, the first and second retinal images 10a, 10b show the optic disc 1 and vasculature 2 of the retina 3.

The second step 200 of the method is to reduce the size of the first and second digital vascular image data. This is achieved by down sampling the data. In the embodiment of the invention described here the first and second digital vascular image data is down sampled via a pyramid scaling computation. However, it should be appreciated that other known filtering, smoothing, sampling or sub sampling computation method could be used.

Reducing the size of the first and second digital vascular image data increases the speed of subsequent computations and scales the vasculature features so that an optimum degree of resonance occurs during subsequent convolution operations (described below). The down sampling scales the vasculature so that the typical curvature, and hence microcorners, are within the area of interest, i.e. so that the best "resonance" is achieved of the corner detection filter, or kernel.

The third step 300 of the method is to optimise the contrast between the vasculature and the background of the first and second digital vascular image data. This is achieved through use of a histogram equalisation computation. In the embodiment of the invention described here an adaptive histogram equalisation is used to optimise the contrast between the vasculature and the background of the first and second digital vascular image data. The adaptive histogram equalisation attenuates variations in general lighting in the image data while increasing local contrast. This has the effect of accentuating vasculature relative to the image background. This effect is most notable in regions where polarisation effects would otherwise tend to swamp out vasculature information.

The fourth step 400 of the method is to remove noise from the first and second digital vascular image data which appears through use of the adaptive histogram equalisation. Removal of this noise reduces the chances of recording false "corner hits" during subsequent convolution operations (described below). The step of removing noise from the first and second digital vascular image data is achieved by a low pass (LP) noise filter.

Figure 3A:
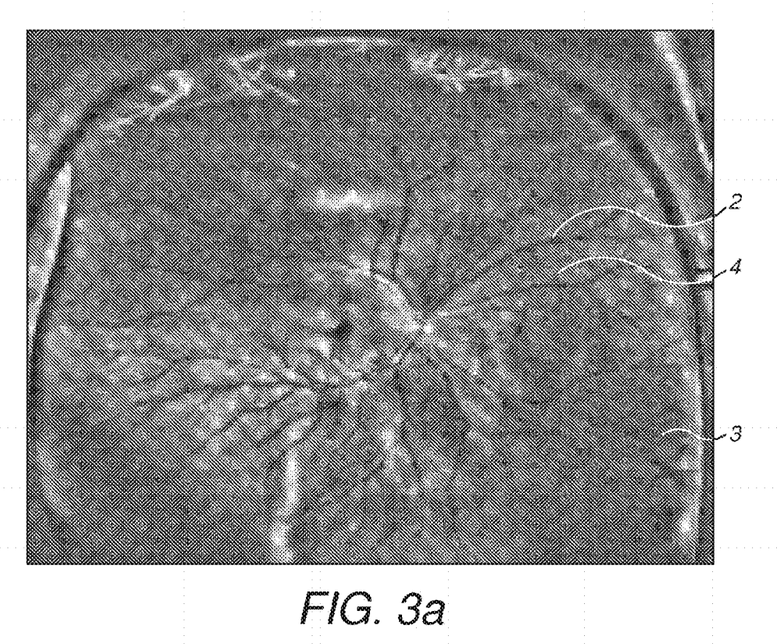
FIGS. 3a and 3b are the first and second digital vascular images of FIGS. 2a and 2b after down sampling, equalisation and filtering.
Figure 3B:
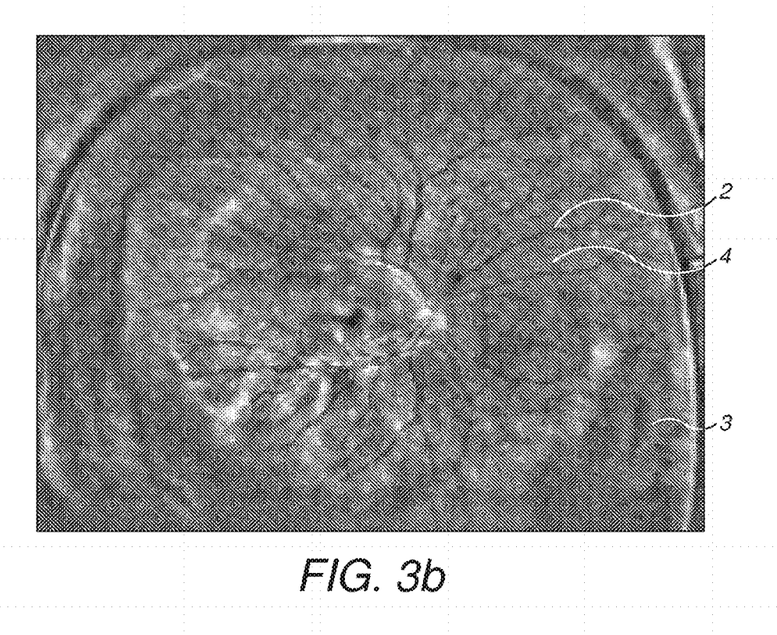

FIGS. 3a and 3b are the first and second digital vascular images 10a, 10b of FIGS. 2a and 2b after down sampling (step 200), equalisation (step 300) and noise reduction (step 400). As can be seen from FIGS. 3a and 3b, the contrast between the vasculature 2 and the background 4 of the retina has been enhanced compared to the initial first and second digital retinal images 2a, 2b. The enhancement of the vasculature 2 relative to the background 4 of the retina improves the results of the subsequent convolution operations (described below).

The fifth step 500 of the method is to process the first and second image data with a directional filter that has the effect of producing clusters of orthogonally adjacent image data points in which the intensity gradient between each orthogonally adjacent image data point is less than a predetermined value. In the embodiment of the invention described here the step 500 of processing the first and second image data with a directional filter is carried out by convolving the first and second image data with a rotating Gabor kernel (or filter). Orthogonally adjacent image data points is considered to mean image data points that are immediately adjacent one another in an array of pixel data, i.e. image data points that are adjacent one another in any given row or column of the array. It should be appreciated that the clusters may comprise any number or configuration of orthogonally adjacent image data. That is, the clusters could be an arrangement 1×1, 1×2, 2×1, 2×2, 3×2, 2×3 image data points, or the like.

The Gabor kernel is a form of 2-dimensional Gaussian filter kernel with a profile that, in the present case, is matched to the form or shape of the intensity of the image data across the vasculature, i.e. the vasculature cross section. The Gaussian shape of the Gabor kernel allows it to "fit" to or "resonate with" the profile of the vasculature, thus accentuating the vasculature, while not fitting as well to other (background) regions, thus attenuating these regions.

The Gabor kernel is convolved with each of the first and second image data a multiple number of times. For each successive convolution the Gabor kernel is oriented differently relative to the image data. In the embodiment described here the Gabor kernel is effectively convolved eight times with each of the first and second image data, with the Gabor kernel being rotated 45 degrees relative to the image data for each successive convolution. The Gabor kernel is therefore rotated through 360 degrees relative to the image data over 8 convolutions. The Gabor kernel has been found to be particularly effective in resonating with the characteristics of the vasculature cross sections. In an embodiment where the kernel is symmetrical, the effect of 8 convolutions over 360 degrees can be achieved in practice with only four convolutions spaced over 180 degrees.

Figure 4A:
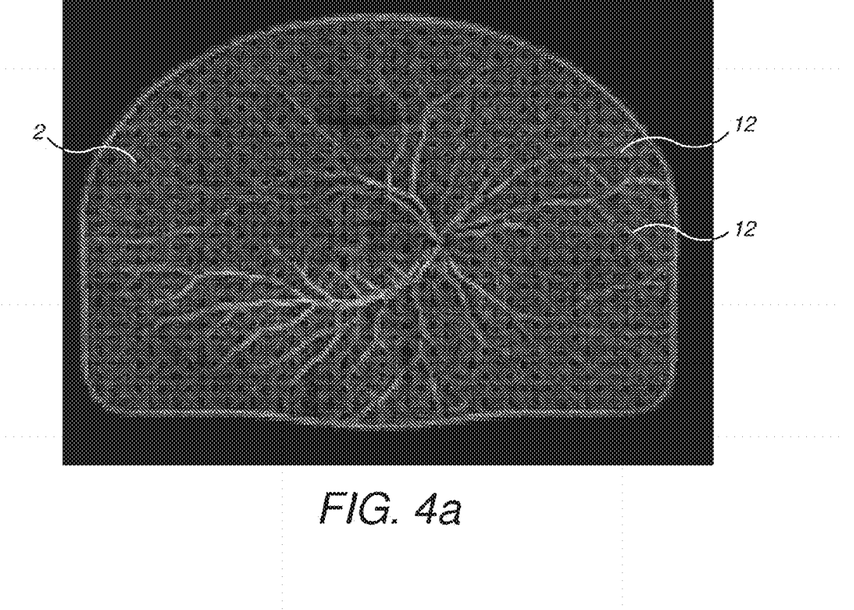
FIGS. 4a and 4b are the first and second digital vascular images of FIGS. 3a and 3b after convolution with a rotating Gabor kernel.
Figure 4B:
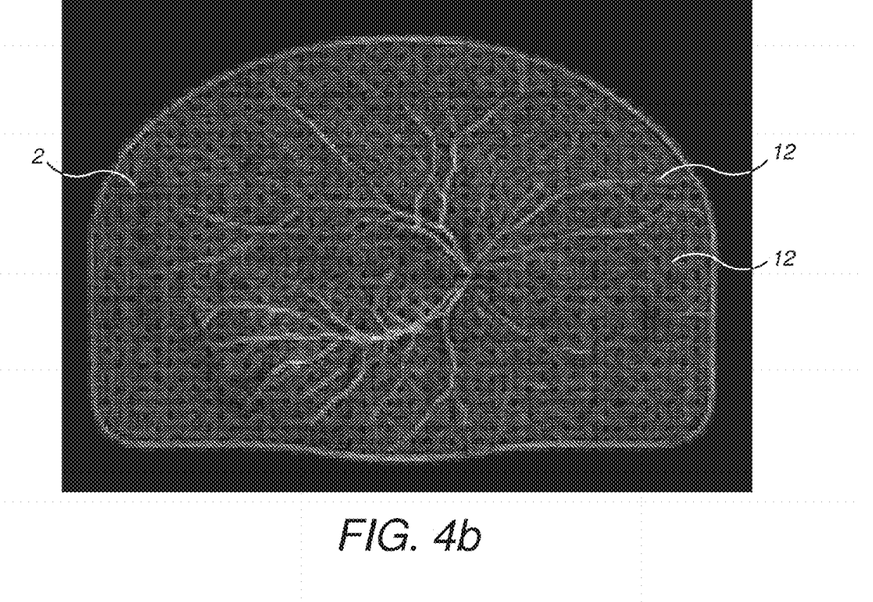

The first and second digital retinal image data after convolution with the rotating Gabor kernel is represented in FIGS. 4a and 4b. FIGS. 4a and 4b represent an averaged output of all 8 convolutions. As illustrated, the effect of convolving the first and second digital retinal image data with the rotating Gabor kernel described above is to produce clusters 12 of orthogonally adjacent image data points in which the magnitude of the intensity gradient between each orthogonally adjacent image data point is less than a predetermined value. The convolution in other words produces groups of orthogonally adjacent image data points that have similar intensity values.

With reference to FIGS. 4a to 6, the first and second digital retinal image data after convolution with the rotating Gabor kernel includes a line of clusters 12 having corner (or "micro-corner") features can be seen that track the vasculature 2 of the retina 3. It is the rotation of the Gabor kernel relative to the image data which creates the corner (or micro-corner) features of the clusters 12. In particular, it is the rotation of the Gabor kernel through, at least, 90 degrees which creates the corner (or micro-corner) features of the clusters 12.

The vasculature 2 of the retina 3 has thus been enhanced at a local level into the form of a high intensity gradient "stepping" structure of corner (or micro-corner) features of the clusters 12 between the clusters 12 and the background 4 of the retina 3. The corner features of the clusters 12 may be any corner of the array of image data, as described above. The term "micro-corner" may refer to a cluster 12 comprising of a 1×2 or 2×1 image data points.

The sixth step 600 of the method is to identify (or extract) the clusters 12 in each of the first and second image data where the magnitude of the intensity gradient between one or more adjacent clusters 12 is above a predetermined value. The sixth step 600 thus identifies clusters 12 that approximately lie on the boundary between the vasculature 2 of the retina 3 and the background 4. As illustrated in FIGS. 4a to 6, the clusters 12 have a higher intensity than the background 4. Step 600 of the method thus identifies the clusters 12 that track the vasculature 2 of the retina 3.

In the embodiment of the invention described here the step 600 of identifying the clusters 12 in each of the first and second image data where the magnitude of the intensity gradient between one or more adjacent clusters 12 is above a predetermined value is carried out by using a corner detection algorithm. In the embodiment described here a Harris corner detection algorithm is used to identify the clusters 12 in each of the first and second image data where the magnitude of the intensity gradient between one or more adjacent clusters 12 is above a predetermined value. However, it should be appreciated that any other suitable corner detection algorithm could be used.

Figure 6:
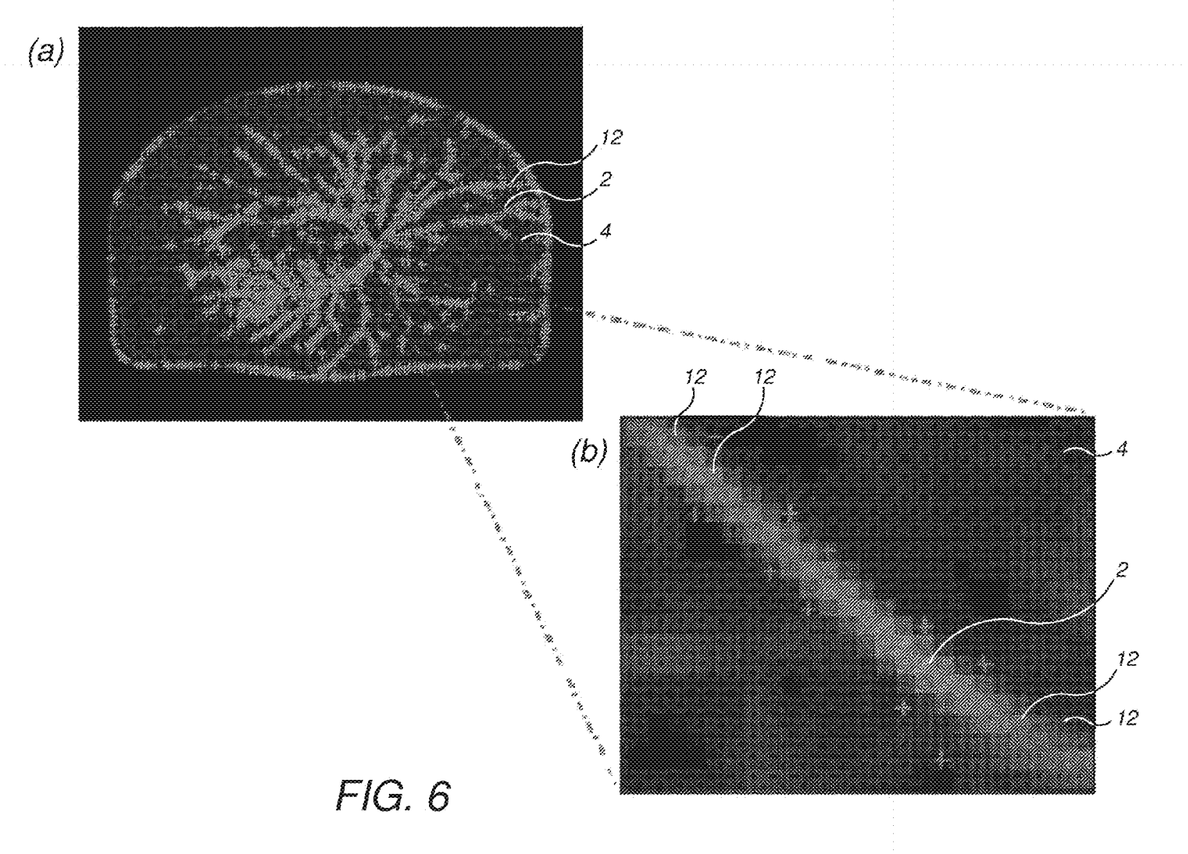
FIG. 6 is the first digital vascular image of FIG. 5a after identification and marking of the micro-corner stepping structure.

The corner detection algorithm looks for orthogonal edge points in the convolved first and second digital retinal image. In particular, it will look for points where the gradient exceeds the threshold in two directions simultaneously. The algorithm is configurable to certain sensitivity and quality thresholds, as required. FIG. 6 illustrates points (+) identified by the corner detection algorithm.

Corner detection algorithms are not typically used with retinal images, since the existence of corner points is not commonly found. However, the pre-processing of the image data with a directional filter such as the rotating Gabor kernel results in image data in which the vasculature 2 has been enhanced at a local level in the form of a high intensity gradient "stepping structure", or lines of corner (or micro-corner) features throughout the vasculature 2. It is this pre-processing with the rotating Gabor kernel which facilitates use of a corner detection algorithm to identify the clusters 12 that outline the vasculature 2 of the retina 3. The advantage of this method, when compared to mapping and extracting the vasculature by use of known tracking algorithms, is a significant decrease in computational loading.

Because the image data has been histogram equalised, the intensity gradient thresholds that are of interest will be approximately the same over the whole image data. The value of the predetermined threshold will be dependent on the size of the area of interest used in the equalisation. Setting the actual value need not be done by any analytical method, but may simply be done by trial and error empirical means. In some embodiments, the threshold may be for example between 10% and 50% of the maximum possible gradient. For example, in an embodiment where the maximum gradient is 255, a threshold gradient of 50 might be set, representing about 20% of the maximum possible.

The seventh step 700 of the method is to merge together the clusters 12 in each of the first and second image data where the magnitude of the intensity gradient between one or more adjacent clusters 12 is above a predetermined value. The seventh step 700 thus blurs, or merges, the clusters 12 together to further highlight the vasculature 2. When the image data is represented in an image the effect of the seventh step 700 is to "join the dots" of the clusters 12 along the vasculature 2. Step 700 of the method is useful since the positioning of the clusters 12 in each image data could be slightly different, therefore merging the clusters 12 increases the chance that more clusters 12 overlap at characteristic positions. The vasculature corner points that have been "thresholded" from the image are still in greyscale form, i.e. each data point could still have a different intensity value, although all are above the threshold value. The method may therefore include the further step of converting the "thresholded" image data to a binary image in which all "corner" clusters have a value of 1 and all the other image data points have a value of 0.

The eighth step 800 of the method is to mask clusters 12 in the image periphery that may be attached to non-relevant features, such as eye lashes.

The ninth step 900 of the method is to reduce the size of first and second merged cluster image data. This is achieved by down sampling the data. In the embodiment of the invention described here the first and second digital vascular image data is down sampled via a pyramid scaling computation. However, it should be appreciated that other known filtering, smoothing, sampling or sub sampling computation method could be used.

Figure 5A:
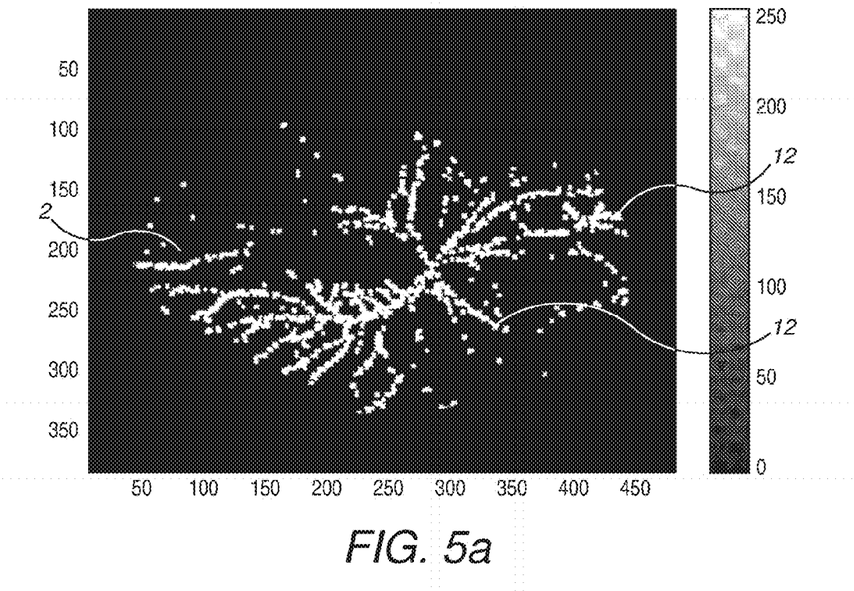
FIGS. 5a and 5b are the first and second digital vascular images of FIGS. 4a and 4b after processing with a corner detection algorithm, blurring and down sampling.
Figure 5B:
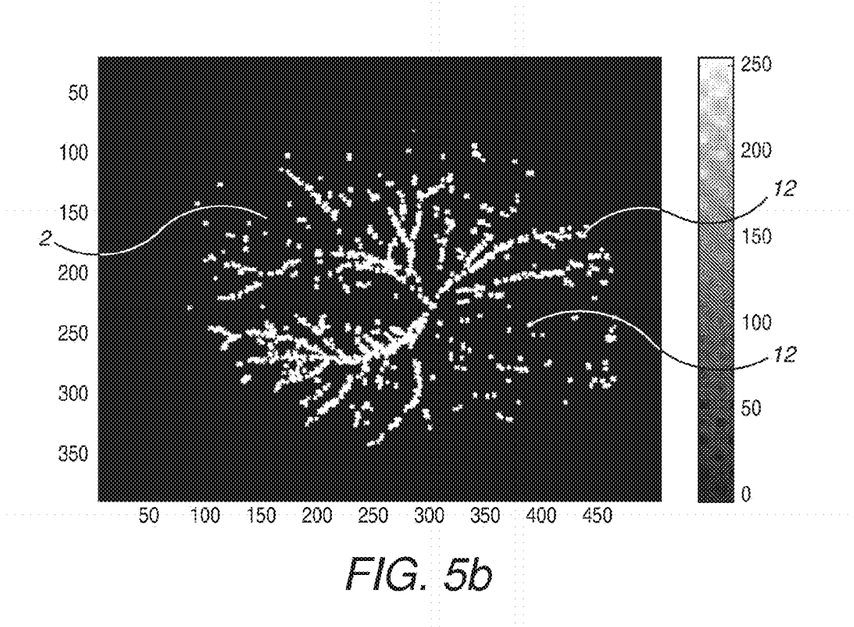

The first and second retinal image data after merging (step 700), masking (800) and down sampling (900) is represented in FIGS. 5a and 5b.

The tenth step 1000 of the method is to identify common clusters 12 between the first and second image data where the magnitude of the intensity gradient between one or more adjacent clusters 12 is above a predetermined value. The tenth step 1000 thus identifies common clusters 12 between each of the first and second retinal image data. In the embodiment described here the step 1000 involves cross correlating the image data of FIGS. 5a and 5b.

Figure 7:
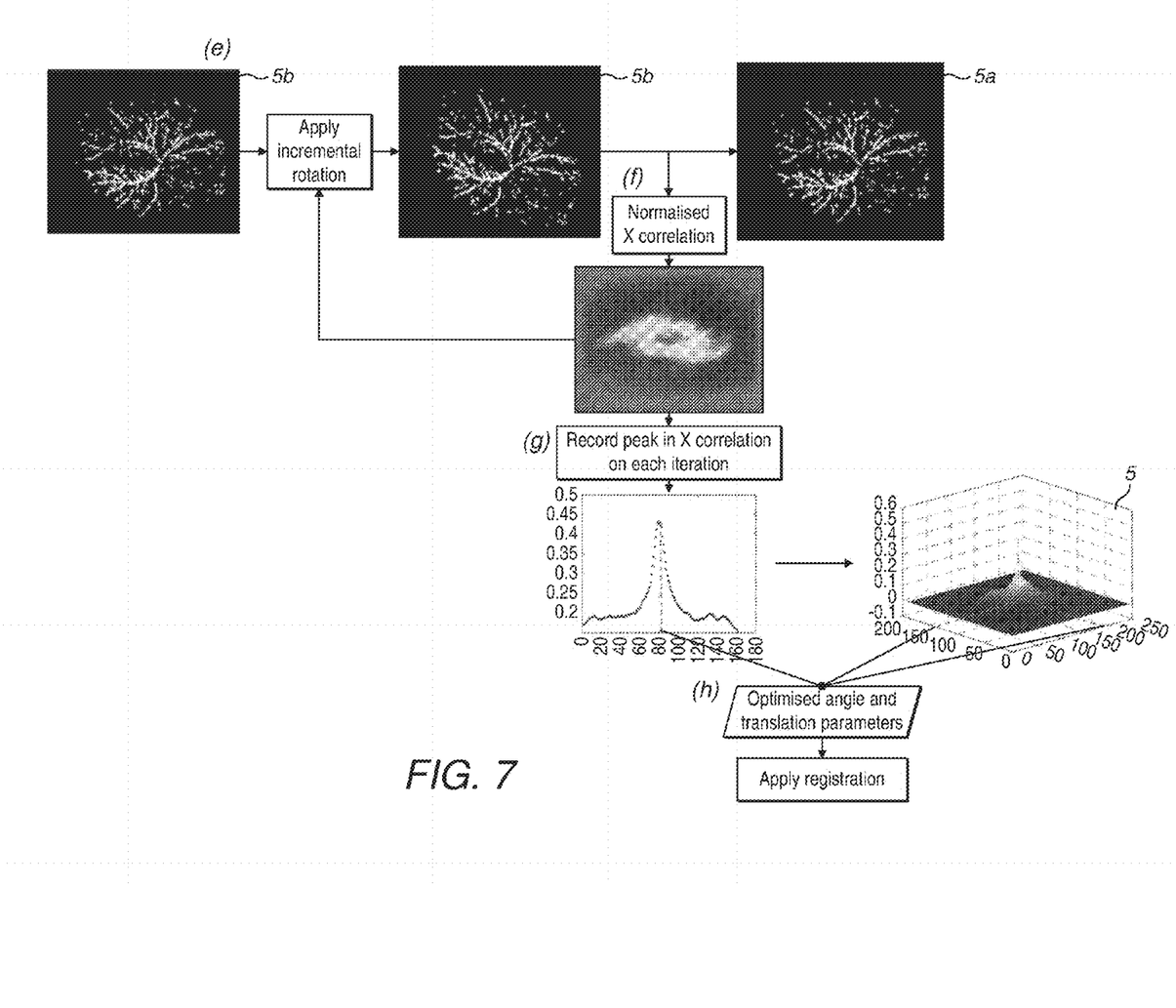
FIG. 7 is a schematic diagram detailing the cross correlation of the first and second digital vascular images of FIGS. 5a and 5b.

The cross correlation of the image data of FIGS. 5a and 5b is illustrated in FIGS. 7 and 1. In the embodiment described here the second image data of FIG. 5b is cross correlated with the first image data of FIG. 5a a number of times. With each subsequent cross correlation the second image data is incrementally rotated relative to the last. The multiple cross correlations may be rotated through approximately 40 degrees. The multiple cross correlations may be rotated through approximately 20 degrees around a pivot point located substantially around the optic disc point of the retina. The multiple cross correlations may, of course, be rotated through approximately any suitable degree around the pivot point located substantially around the optic disc point of the retina.

Data is output as a normalised cross correlation. The peak in cross correlation (i.e. best match between image data) is recorded for each correlation angle and confidence is deduced from a measurement of the peak isolation within the correlation surface 5 for each correlation angle. More specifically, a confidence coefficient is calculated as a weighting of the peak height multiplied by the total slope of the peak "walls" divided by the mean of the rest (i.e. excluding the region of the peak) of the correlation surface 5. A high value in this metric is indicative of a sharp, high, isolated peak, which is a characteristic of close correlation and therefore a high confidence in the accuracy of registration. The threshold at which confidence is toggled to low, which can be observed as an absence in any one isolated correlation peak, is established by weighting the confidence measure so that values less than unity indicate low confidence.

The tenth step 1000 of the method also includes determining the differences in position between the identified common clusters 12 in each of the first and second image data. The position of the cluster 12 includes its angular and translational position (rotational angle and x and y translations). The differences in position between the identified common clusters 12 in each of the first and second image data is termed the translational parameters.

The eleventh step 1100 of the method is to register the common clusters 12 between the first and second image data. Here the translation parameters determined from step 1000 are used to align the second image data to the first image data, or align the first and second digital retinal images 10a, 10b, in the known manner.

Figures 8, 8A:
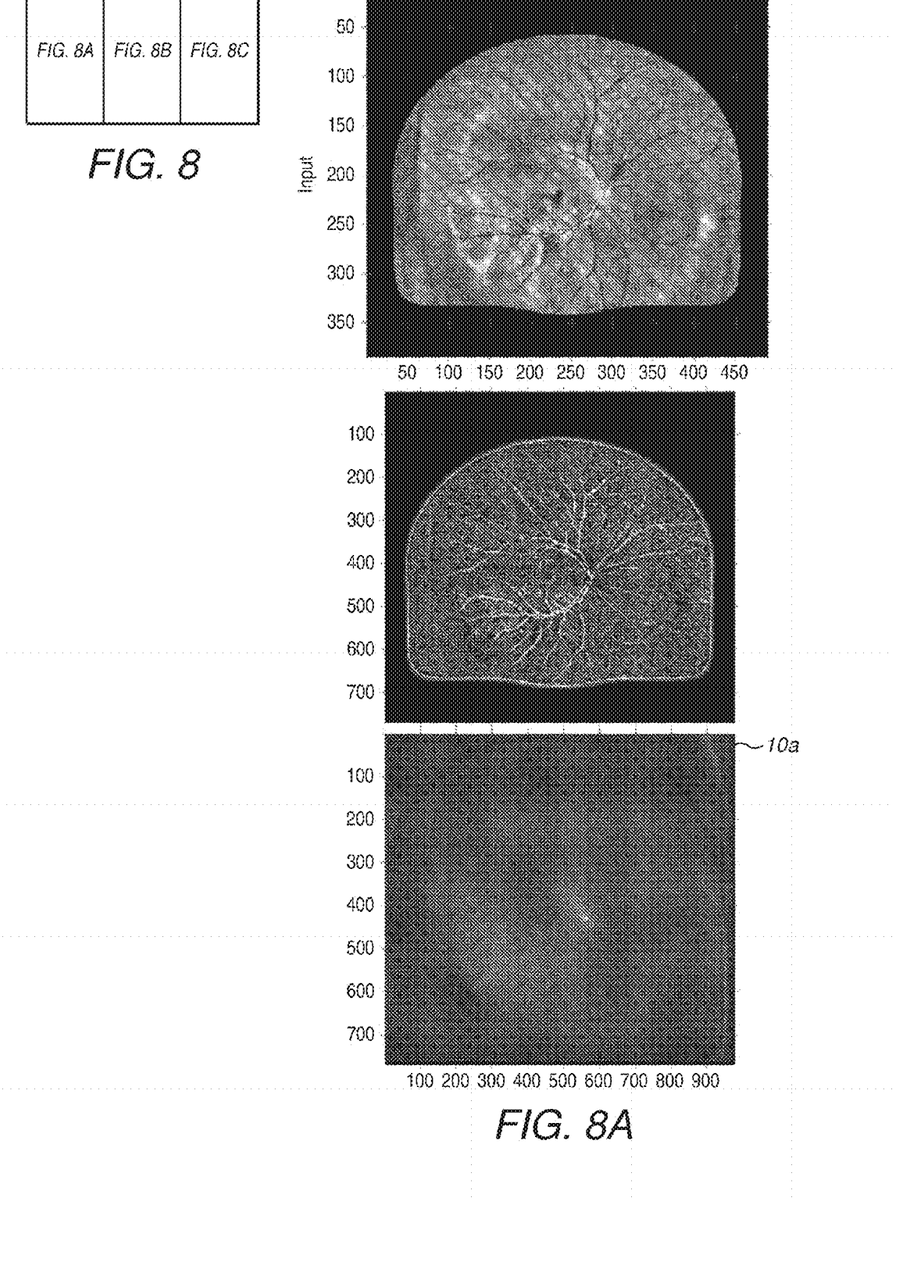
FIG. 8 illustrates the digital vascular images produced during the processing method and the registered first and second digital vascular images.
Figure 8B:
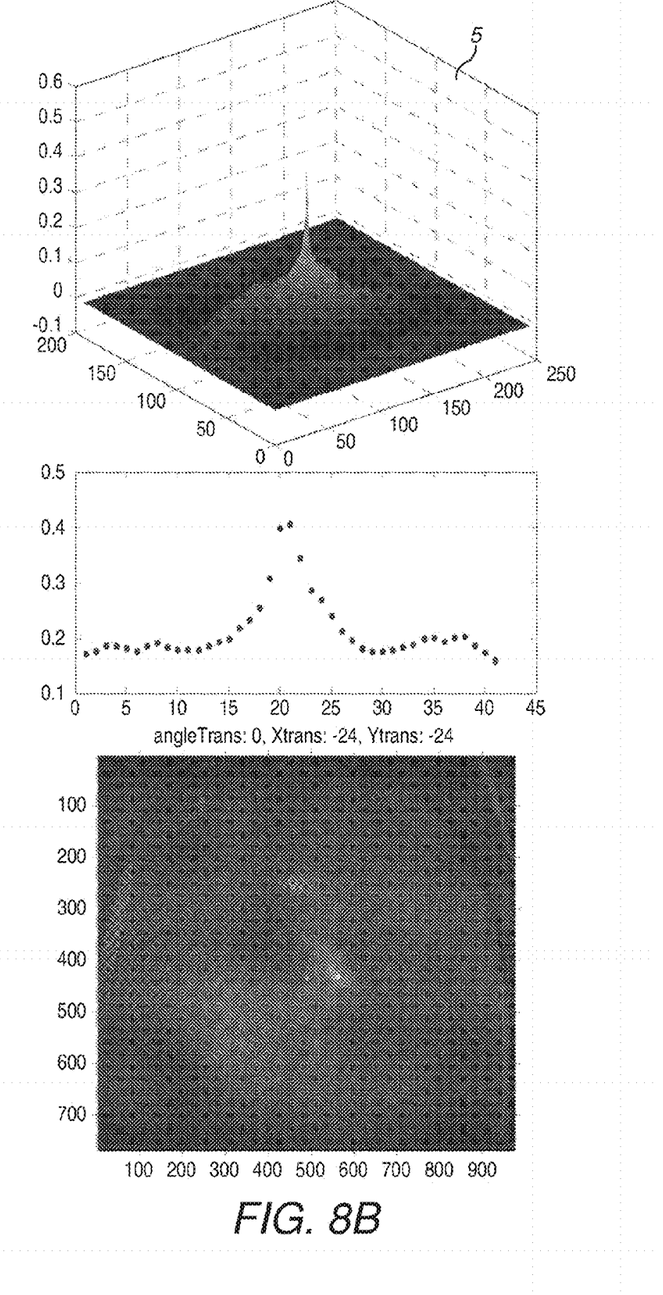
Figure 8C:
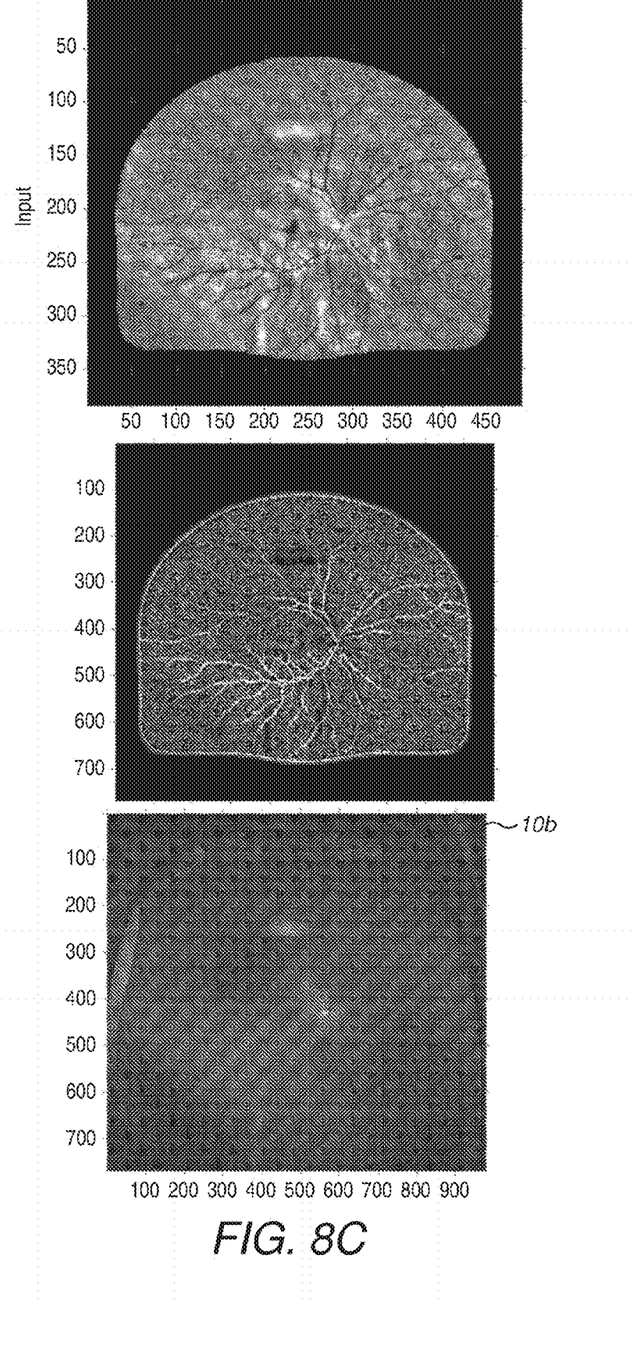

FIG. 8 illustrates the digital vascular images produced during the processing method and the registered first and second digital vascular images 10a, 10b. Top-left and top right of FIG. 8 illustrate the first and second digital vascular images 10a, 10b of FIGS. 2a and 2b after down sampling (step 200), equalisation (step 300) and noise reduction (step 400) (FIGS. 3a and 3b). Middle-left and middle-right of FIG. 8 illustrate the first and second digital retinal image data after convolution with the rotating Gabor kernel (FIGS. 4a and 4b). Bottom-left and bottom-right of FIG. 8 illustrate the first and second digital vascular images 10a, 10b in their registered positions. The centre-top of FIG. 8 is the correlation surface 5 of FIG. 7. The centre-middle of FIG. 8 illustrates the peak in cross correlation for each correlation angle. The bottom-middle of FIG. 8 illustrates the registered and overlaid first and second digital vascular images 10a, 10b.

The method of the invention dramatically reduces the computational requirements of the processor, increases accuracy and allows registration for images obtained across a number of imaging modes. The computational efficiency provided by the method of the invention is a result of the realisation that convolving the image data with a rotating Gabor kernel produces image data in which the vasculature has been modified to provide a high intensity gradient "stepping" structure of image data clusters that track the vasculature. The creation of these corner (or micro-corner) features in the image data facilitates the use of a known corner detection algorithm to extract the position of the clusters for comparison and registration. Convolving the image data with a rotating Gabor kernel and using a corner detection algorithm in this manner reduces the computational requirements of the method. Furthermore, using a corner detection algorithm increases the accuracy of the registration process, since the corners (and vasculature) can be accurately determined compared to known retinal image registration techniques.

Also, since the method uses feature sets (distances between vasculature points) that are common across different retinal imaging modes (e.g. reflectance, auto-fluorescence etc.), inter-mode registration (i.e. auto-fluorescence to reflectance images) is possible.

Modifications and improvements may be made to the above without departing from the scope of the present invention. For example, although the method has been described and illustrated with use of retinal images, it should be appreciated that other digital vascular images may be used, such as vascular images of an organ or body part of a human or an animal. The vasculature of the organ or the body part may include the blood vessels arteries and veins therein. The vasculature of the organ or the body part may also include the circulatory system thereof.

Furthermore, although the method has been described with use of a Gabor kernel, it should be appreciated that any suitably shaped kernel, filter, filter matrix, window, template or mask may be used. For example a Gaussian filter or kernel may be used. Also, although a rotating Gabor kernel has been described that rotates through 360 degrees (with eight convolutions), it should be appreciated that the kernel need not "rotate", it need only be convolved with the image data in two orthogonal dimensions (i.e. a first convolution and then a second convolution at an angle of 90 degrees from the first). Rotating the kernel through 360 degrees does, however, improve the enhancement of the vasculature, as described above, and is preferred. Furthermore, although the method has been described above as using a single kernel convolved with the image data a number of times, it should be appreciated that any number of different kernels could be convolved with the image data at any number of angles relative thereto.

Also, although the method has been described and illustrated above as registering two retinal images, it should be appreciated that the method may comprise the step of providing a plurality of digital vascular image data (and a plurality of digital vascular images) and processing each digital image according to the above described method to register all image data and images.

The invention claimed is:

1. A method of processing digital vascular images, the method comprising the steps of:
    providing first and second digital vascular image data;
    processing the first and second image data with a two-dimensional, directional filter that has the effect of producing clusters of orthogonally adjacent image data points in which the magnitude of an intensity gradient between each orthogonally adjacent image data point is less than a predetermined value;
    identifying clusters in each of the first and second image data where the magnitude of the intensity gradient between at least one adjacent cluster is greater than a predetermined value;
    identifying common clusters between the first and second image data where the magnitude of the intensity gradient between at least one adjacent cluster is greater than a predetermined value; and
    registering the common clusters between the first and second image data.

2. The method as claimed in claim 1, wherein the step of processing the first and second image data with said directional filter includes multiple convolutions of the image data with at least one filter kernel, the at least one filter kernel being oriented differently for each convolution.

3. The method as claimed in claim 2, wherein the filter is incrementally rotated relative to the image data for each successive convolution.

4. The method as claimed in claim 2, wherein the filter is effectively rotated through 360 degrees relative to the image data over a number of convolutions.

5. The method as claimed in claim 1, wherein the directional filter is a Gabor filter.

6. The method as claimed in claim 1, wherein the step of identifying clusters in each of the first and second image data where the magnitude of the intensity gradient between at least one adjacent cluster is above a predetermined value includes use of a corner detection algorithm.

7. The method as claimed in claim 6, wherein the corner detection algorithm is operates by identifying clusters in each of the first and second image data where the magnitude of the intensity gradient between at least one adjacent cluster in two orthogonal directions is simultaneously above said predetermined value.

8. The method as claimed in claim 6, wherein the predetermined value is between 10% and 50% of a maximum possible gradient value.

9. The method as claimed in claim 1, wherein the step of identifying common clusters between the first and second image data where the magnitude of the intensity gradient between at least one adjacent cluster is above a predetermined value includes cross correlating the convolved first and second image data.

10. The method as claimed in claim 1, wherein the step of identifying common clusters between the first and second image data where the magnitude of the intensity gradient between at least one adjacent cluster is above a predetermined value includes cross correlating the identified clusters in the first and second image data.

11. The method as claimed in claim 1, wherein the step of identifying common clusters between the first and second image data where the magnitude of the intensity gradient between at least one adjacent cluster is above a predetermined value includes multiple cross correlations of the convolved first and second image data with different orientations.

12. The method as claimed in claim 11, wherein the multiple cross correlations are rotated in steps through approximately 20 degrees or more around a pivot point located substantially around the optic disc point of the retina.

13. The method as claimed in claim 10, wherein the step of cross correlating the convolved first and second image data includes the further step of determining differences in position between the identified common clusters in each of the first and second image data.

14. The method as claimed in claim 13, wherein the position of the cluster includes its angular position and/or its translational position, the differences in position between the identified common clusters in each of the first and second image data being termed the translational parameters, wherein the step of registering the common clusters between the first and second image data uses the determined translational parameters to align the first and second image data.

15. The method as claimed in claim 1, wherein the method includes the step of merging clusters in each of the first and second image data where the magnitude of the intensity gradient between at least one adjacent cluster is above a predetermined value.

16. The method as claimed in claim 1, wherein an averaging filter is used to adjust the intensity value of the image data between clusters to an average intensity value of the clusters in that region.

17. The method as claimed in claim 1, wherein the method includes the step of creating first and/or second digital vascular images from the first and second digital vascular image data.

18. The method as claimed in claim 1, wherein the method includes the step of creating a digital image of the registered common clusters between the first and second image data.

19. The method as claimed in claim 1, comprising providing a plurality of digital vascular image data and processing each digital image data to register all the common clusters between all the image data.

20. The method as claimed in claim 1, wherein the digital vascular images are vascular images of an organ or a body part of a human or an animal.

21. The method as claimed in claim 1, wherein the digital vascular images are retinal images of a human or an animal.

22. The method as claimed in claim 20, wherein said digital vascular images are images obtained using different modes of imaging.

23. A An image processing apparatus comprising:
   a digital vascular image provision module arranged to provide first and second digital vascular image data; and
   a processor configured to
      provide first and second digital vascular image data;
      process the first and second image data with a two-dimensional,
   directional filter that has the effect of producing clusters of orthogonally adjacent image data points in which the magnitude of an intensity gradient between each orthogonally adjacent image data point is less than a predetermined value;
      identify clusters in each of the first and second image data where the magnitude of the intensity gradient between at least one adjacent cluster is greater than a predetermined value;
      identify common clusters between the first and second image data where the magnitude of the intensity gradient between at least one adjacent cluster is greater than a predetermined value; and
   register the common clusters between the first and second image data.

24. A scanning laser ophthalmoscope comprising: an image processing apparatus comprising
   a digital vascular image provision module arranged to provide first and second digital vascular image data; and
   a processor configured to
      provide first and second digital vascular image data
      process the first and second image data with a two-dimensional,
   directional filter that has the effect of producing clusters of orthogonally adjacent image data points in which the magnitude of an intensity gradient between each orthogonally adjacent image data point is less than a predetermined value;
      identify clusters in each of the first and second image data where the magnitude of the intensity gradient between at least one adjacent cluster is greater than a predetermined value;
      identify common clusters between the first and second image data where the magnitude of the intensity gradient between at least one adjacent cluster is greater than a predetermined value; and register the common clusters between the first and second image data.

25. A non-transitory computer program product encoded with instructions that, when run on a computer, cause the computer to provide first and second digital vascular image data;

process the first and second image data with a two-dimensional, directional filter that has the effect of producing clusters of orthogonally adjacent image data points in which the magnitude of an intensity gradient between each orthogonally adjacent image data point is less than a predetermined value;

identify clusters in each of the first and second image data where the magnitude of the intensity gradient between at least one adjacent cluster is greater than a predetermined value;

identify common clusters between the first and second image data where the magnitude of the intensity gradient between at least one adjacent cluster is greater than a predetermined value; and register the common clusters between the first and second image data.

* * * * *